United States Patent [19]

Asp

[11] 4,361,646
[45] Nov. 30, 1982

[54] METHOD FOR DETERMINING BOTH WATER-INSOLUBLE AND WATER-SOLUBLE PLANT FIBRE COMPONENTS IN PLANT MATERIAL

[75] Inventor: Nils-Georg Asp, Lund, Sweden

[73] Assignee: Tecator AB, Haganas, Sweden

[21] Appl. No.: 216,997

[22] PCT Filed: Mar. 26, 1979

[86] PCT No.: PCT/SE79/00066

§ 371 Date: Nov. 26, 1980

§ 102(e) Date: Nov. 24, 1980

[87] PCT Pub. No.: WO80/02075

PCT Pub. Date: Oct. 2, 1980

[51] Int. Cl.³ .................... C12Q 1/00; G01N 31/00
[52] U.S. Cl. .................................... 435/4; 435/22; 435/23; 23/230 M
[58] Field of Search ...................... 435/277–279, 435/311, 4, 22, 23; 23/230 B, 230 M

[56] References Cited

U.S. PATENT DOCUMENTS 1,808,593 6/1931 Clark ............................. 435/278
2,046,940 7/1936 Fitger et al. ................... 23/230 M

FOREIGN PATENT DOCUMENTS 2000695 1/1979 United Kingdom .

Primary Examiner—Thomas G. Wyse
Attorney, Agent, or Firm—Bucknam and Archer

[57] ABSTRACT

For determining both water-insoluble and water-soluble plant fibre components in plant fibre material, more particularly dietary fibre components in dietary plant material, a sample which has been solubilized and degraded with regard to other plant components is passed through a glass filter (2) capable of retaining the water-insoluble fibre components of the sample and then through an ultrafilter (1) capable of retaining the water soluble fibre components and the sample.

6 Claims, 1 Drawing Figure

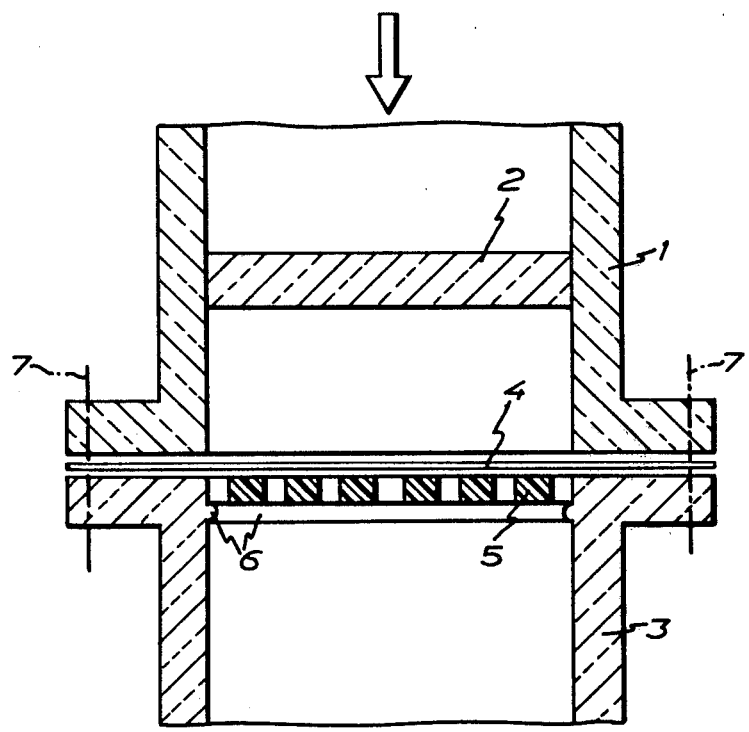

METHOD FOR DETERMINING BOTH WATER-INSOLUBLE AND WATER-SOLUBLE PLANT FIBRE COMPONENTS IN PLANT MATERIAL

The invention relates to a method and an apparatus for determining both water-insoluble and water-soluble plant fibre components in plant material.

Dietary fibre or fibres are defined as those constituents of vegetable foodstuffs which withstand digestion by enzymes produced in the human oral cavity, stomach and small intestine and therefore pass in an unchanged state into the large intestine. During the 1970's, an ever increasing interest was devoted to dietary fibres in terms of research and discussion of the importance of diet to health. Hypotheses have been put forth to the effect that a low intake of dietary fibres would imply a considerable risk factor for being inflicted with various diseases usual in affluent societies.

From a chemical aspect, dietary fibres include water-insoluble substances (such as cellulose, hemicellulose, lignin) and water-soluble substances (such as pectin, inulin, certain hemicellulose). Additives to plant-based food products, such as alginates, carrageenans, vegetable gums and carboxymethyl cellulose, are also included in the dietary fibre concept.

Of fundamental importance to research and development work concerning dietary fibres is to have the use of a suitable routine method of analysis for determining the dietary fibre contents in raw materials, ready-to-consume foodstuffs, and mixed food samples from investigations of food habits. The routine methods of analysis hitherto published are all based on the sample being pretreated such that the other components are solubilized by chemical degradation ("crude fibre", Official Methods of AOAC, 1975, 136), or by treatment with wetting agents ("neutral detergent fiber/acid detergent fiber", van Soest and Wine, J. AOAC, 1967, 50, 50), or by enzymatic degradation (Weinstock and Benham, J. Cereal Chem., 1951, 28, 490; Hellendoorn et al., J. Sci, Food Agric., 1975, 26, 1461).

Dietary fibres are then separated by filtration of the sample through a glass filter. As glass filters have large pores, water-soluble dietary fibre components will obviously get lost, for which reason all of the aforementioned methods yield dietary fibre values which only comprise water insoluble components.

The object of the invention is to provide a method and an apparatus which permit determining both water-insoluble and water-soluble plant fibre components, particularly dietary fibre components in plant material, and which as a consequence give a more correct total fibre value than the prior art techniques outlined above.

This object is attained according to the present invention by a method and an apparatus having the characteristic features defined in the appended claims.

In short, the invention aims at solubilizing the water soluble fibre components of the plant fibre material and degrading and solubilizing the non-fibre components of the plant material, whereupon said material is filtered through a filter, such as a glass filter, which retains the water-insoluble fibre components, and then through an ultrafilter or membrane filter which retains the water-soluble fibre components but passes the decomposed non-fibre components.

An embodiment of the invention will be described in greater detail below with reference to the accompanying drawing illustrating an apparatus according to the invention in section.

To the plant-based sample, such as a sample of a vegetable food product, whose water soluble and water insoluble plant fibre or dietary fibre components shall be determined, there are supplied substances or organisms capable of degrading or splitting large-molecular organic non-fibre components, such as protein and starch, into smaller fragments or molecules, such as amino acids and sugar, respectively, said non-fibre components thus constituting the nutritively available constituents of vegetable diet. For the purpose of degradation, use is advantageously made of enzymes of the type conventionally utilized for dietary fibre determination by enzymatic degradation, i.e. amylase for starch degradation and proteinase for protein degradation, and said enzyme-based degradation is performed in conventional manner by introducing the sample of determined weight, a buffered aqueous solution of suitable pH for enzymatic degradation, and the enzymes into a flask. The buffer solution solubilizes the water soluble plant or dietary fibre components and the degraded non-fibre components. The degrading action of the enzymes is accelerated in the usual manner by heating of the sample in the flask. If necessary, the weighed sample can be extracted with fat before the above-mentioned procedure is performed.

The flask contents are filtered after terminated enzymatic degradation in the usual manner through a glass filter 2 which retains the water-insoluble fibre components of the plant material and passes the water soluble fibre components thereof, such as pectine, inulin and certain hemicellulose as well as the proteins degraded by the enzymes, and the starch. After filtration, the plant fibre components that according to the earlier technique constituted the basis of the total fibre determination, are to be found on the glass filter.

According to the present invention, it has been found that the conventionally degraded non-fibre components, such as protein and starch, are of such a molecular size that they, or the majority thereof, can pass through an ultrafilter or a membrane filter 4 while the water-soluble fibre components are of such a molecular size as not to pass through the ultrafilter or membrane filter. To exploit said observation for determination of the water-soluble fibre components of a plant material, which could not earlier be determined, the filtrate coming from the glass filter is conducted through an ultrafilter or membrane filter which thus retains the water-soluble fibre components, such as pectin, inulin and certain hemicellulose, and passes the protein and starch fragments obtained by enzyme action.

The requisite pressure on the sample solution for the operation of the ultrafiltration or membrane filtration is brought about by pressure above atmospheric upstream or vacuum downstream of the two filters 2 and 4.

An apparatus for realizing the above described collection of both water-insoluble and water-soluble fibre constituents is illustrated slightly schematically in the accompanying drawing. The important component parts of the apparatus, i.e. a conventional glass filter 2 and a ultrafilter 4, have already been mentioned in the foregoing.

A glass tube 1 contains the glass filter 2 which is attached for instance by melting to the inner wall of the glass tube in conventional manner. A flat membrane 4 is tightly clamped between the lower end surface of the glass tube 1 and the upper end surface of another glass tube 3. Said membrane is supported by a plastics insert 5 which in turn is carried by a bead 6 integral with the inner wall of the glass tube 3. The clamping of the glass tubes 1 and 3 can be realized in any manner known to those skilled in the art, for example with the aid of screws or clamps, the clamping means being indicated in the drawing by reference numeral 7. Said clamping means cooperate with outwardly directed flanges on the facing ends of the glass tubes 1 and 3. Other ways in which to mount the ultrafilter 4 in series after the glass filter 2 lie within the range of competence of those skilled in the art. The arrow in the drawing indicates the direction of flow of the sample through the filters.

After finished filtration of the sample through the filters 2 and 4 the residues remaining on the filters 2 and 4 are flushed and dried, whereupon the desired analyses are performed on both the water-insoluble fibre components of the sample, which are retained by the filter 2, and the water-soluble fibre components of the sample, which are retained by the filter 4.

The analysis may aim for instance at determining the weight of said fibre components. In this analysis, either the total fibre contents of the sample can be determined by weighing the glass tubes 1 and 3 in their assembled state, or the contents of the sample of water-insoluble fibre components and water-soluble fibre components, respectively, can be determined by breaking the connection at 7 and separately weighing the glass tubes 1 and 3 with the fibre components retained on the respective filters, whereafter the tara weights of the filter glass tubes are deducted.

I claim:

1. A method of analyzing a dietary plant material in water to determine the water-insoluble and the water-soluble plant fibre components thereof, which comprises the steps of treating a sample of the plant material to degrade non-fibre components thereof and to substantially solubilize in water the degraded non-fibre components and the water-soluble fibre components of the sample; filtering the sample through a first filter adapted to retain water-insoluble fibre components; filtering the sample through a second filter adapted to retain water-soluble fibre components; and determining the amounts of said water-insoluble components and water-soluble components retained by said first and second filters respectively.

2. The method according to claim 1 wherein the degrading of non-fibre components is performed by means of enzymes.

3. The method according to claim 1 or claim 2 wherein the amount of said water-insoluble components retained by said first filter is determined separately from the amount of said water-soluble components retained by said second filter.

4. The method according to claim 1 or claim 2 wherein there is maintained a pressure differential to aid in the filtering of the sample through said first and second filters.

5. The method according to claim 1 or claim 2 wherein said second filter is a membrane filter.

6. The method according to claim 1 or claim 2 wherein said second filter is an ultrafilter.

* * * * *